(12) United States Patent
Sinai

(10) Patent No.: US 9,999,699 B2
(45) Date of Patent: Jun. 19, 2018

(54) CHIP SANITIZING DEVICE

(71) Applicant: Assaf Sinai, Bloomfield, NJ (US)

(72) Inventor: Assaf Sinai, Bloomfield, NJ (US)

( * ) Notice: Subject to any disclaimer, the term of this patent is extended or adjusted under 35 U.S.C. 154(b) by 0 days. days.

(21) Appl. No.: 15/149,266

(22) Filed: May 9, 2016

(65) Prior Publication Data

US 2017/0252477 A1    Sep. 7, 2017

Related U.S. Application Data

(60) Provisional application No. 62/303,629, filed on Mar. 4, 2016.

(51) Int. Cl.
| | |
|---|---|
| *A61L 2/00* | (2006.01) |
| *A63F 11/00* | (2006.01) |
| *A61L 9/20* | (2006.01) |
| *A61L 12/06* | (2006.01) |

(52) U.S. Cl.
CPC .............. *A61L 9/20* (2013.01); *A61L 12/063* (2013.01); *A63F 11/00* (2013.01)

(58) Field of Classification Search
CPC .................................. A63F 11/00; A61L 9/20
USPC .......................................................... 422/24
See application file for complete search history.

(56) References Cited

U.S. PATENT DOCUMENTS

| | | | | |
|---|---|---|---|---|
| 3,906,187 A | * | 9/1975 | Turoczi, Jr. ............. | D06F 75/08 219/245 |
| 5,505,904 A | * | 4/1996 | Haidinger ................ | A61L 9/20 250/435 |
| 8,567,784 B2 | | 10/2013 | Miller et al. | |
| 8,703,051 B2 | * | 4/2014 | Trabalka .................... | A61L 2/10 250/455.11 |
| 9,162,000 B2 | | 10/2015 | Ullman | |
| 9,192,191 B2 | | 11/2015 | Hecht et al. | |
| 2004/0175290 A1 | * | 9/2004 | Scheir ........................ | A23L 3/28 422/24 |
| 2009/0252646 A1 | * | 10/2009 | Holden .................. | A47B 25/00 422/24 |
| 2011/0020175 A1 | * | 1/2011 | Collard ..................... | A61L 2/10 422/24 |

(Continued)

*Primary Examiner* — Kevin Joyner
(74) *Attorney, Agent, or Firm* — Payam Moradian

(57) ABSTRACT

A chip sanitizing device comprises an area that is substantially enclosed and includes a sanitizing unit comprising a germicidal bulb and a power source. One or more chips is placed within the device and after the germicidal bulb is activated the one or more chips is sanitized. In another embodiment of the invention a chip rack is modified to include a sanitizing unit comprising a germicidal bulb, a power source and a fan stored in a housing attached to the chip rack. The slots are modified to contain openings to allow ultraviolet light to reach the chips sitting atop the rack. The ultraviolet light may sterilize microorganisms such as germs and bacterium found on chips. A fan is used to provide circulation and may increase the likelihood of germs and bacteria coming into contact with the ultraviolet light. In a further embodiment of the invention a lid is provided that substantially covers the chip rack and stores the sanitizing unit. In a further embodiment, the inner surfaces of a lid or housing may be covered with reflective material to increase the likelihood that the ultraviolet light comes into contact with germs or bacteria.

20 Claims, 7 Drawing Sheets

(56) References Cited

U.S. PATENT DOCUMENTS

2016/0101202 A1* 4/2016 Gil .................... A61L 2/202
422/186.3

\* cited by examiner

CHIP SANITIZING DEVICE

CROSS REFERENCE TO RELATED APPLICATION

This application claims priority to U.S. provisional patent application Ser. No. 62/303,629 filed on Mar. 4, 2016 the contents of which are hereby incorporated by reference in their entirety into the present application.

BACKGROUND OF THE INVENTION

Field of the Invention

The inventions disclosed within this application are directed to betting games and apparatuses where physical chips are used and stored.

Background of the Prior Art

Every year tens of millions of people from all over the world descend upon casinos in such locales as Las Vegas, Atlantic City, Macau and Monaco in order to gamble their money. They play popular games such as poker, blackjack, craps, roulette and baccarat. These games invariably use chips that correspond with different monetary amounts. The chips are stored on racks at the tables where the different games are played. When a player sits at a table to play a game he may present his chip to indicate the amount he is betting. After a game is completed, these chips can be exchanged with the house or other players, depending on who the winner is.

While these players understand that they risk their money for the potential reward of winning these games, they do not need additional risks to their health based on the germs on the chips. Dealers and other casino employees may be familiar with the risk based on their daily experience with chips in the unique environment found at many casinos and some studies have indicated that such dealers have greater sickness and absence rates than the general population. However, the general public has become increasingly aware of this risk and is concerned with it.

The environment present at casinos is unique and a cause for concern. First, casinos attract large numbers of gamblers from all over the country, and sometimes from all over the world. For example, Las Vegas is ranked as one of the top tourist destination worldwide. The more exotic the visitors, the greater the potential for different bacterium and germs to be found.

Second, the casino floors are a closed environment. Unlike a healthier outdoor setting, casinos do not typically have windows or natural sunlight on the game floors. The casino floors also do not have clean air circulating through them. Natural sunlight can kill some germs in the air and fresh air from outside the casino could replace germs and bacteria.

Researchers have actually inspected different casinos and found empirical evidence of different germs present at Las Vegas casinos. A 2007 study by Bluff Magazine was conducted by collecting chips from different casinos using sterilized gloves. After collecting the chips and allowing them to incubate the researchers inspected them for different microorganisms.

The most common bacterium that the researchers detected was staphylococcus or "staph." It can cause serious skin infections, pimples and boils.

Another germ that was found is *Bacillus anthracis*. This can cause food poisoning.

In light of the foregoing, casinos and gamblers have begun to approach this problem in different ways. First, casinos can wash the chips in different solutions or rub them with alcohol. While this may be feasible to do occasionally before certain key events such as a major gambling competition, it is not something that can be done on a regular basis such as a weekly or monthly basis. Another disadvantage with this approach is that the customer does not know when the chips were last cleaned and therefore may be worried and hesitant to gamble.

Another approach is to provide gamblers with a sterilized latex glove. While this may fit with some cultures in the world it may seem strange to gamblers who have been "regulars" at casinos in the United States and Las Vegas in particular.

A third approach that currently exists involves hand sanitizers. These are ubiquitous in the United States and effective so there would be no hesitation based on cultural norms. However, there is an expense associated with providing and replacing these at every table and therefore gamblers are typically forced to bring their own sanitizer with them.

SUMMARY OF THE INVENTION

Accordingly, there exists a need to sanitize the chips present at casino tables to reduce or eliminate germs, bacterium and micro-organisms that are typically present. It is further desired to provide this sanitation in a transparent manner to assure customers that their chips have been recently sanitized. Additionally, it is beneficial to provide this sanitation in an automated manner to reduce associated costs.

The present invention utilizes ultraviolet light (hereinafter "UV") to sanitize chips and chip racks. UV is electromagnetic radiation and may penetrate the outer cell membrane of a microorganism, break molecular bonds within microorganismal DNA and disrupt the organism's ability to reproduce. The UV light can therefore sterilize the microorganism.

Ultraviolet light corresponds to light with a frequency between 200 nanometers (nm) and 400 nm. UV cannot be seen with the naked eye. The UV spectrum can be divided into three categories UV-A, UV-B, and UV-C.

UV-A or longwave UV light corresponds to the 315 nm to 400 nm range. It is sometimes referred to as "black light."

UV-B or midrange UV corresponds to the 280 nm to 315 nm range and can cause sunburn.

UV-C or germicidal UV light corresponds to the 200 nm to 280 nm range and research has shown that the most efficient frequency for microbial destruction is in the 253 nm to 265 nm range.

In addition to the frequency of the UV light, its effectiveness depends on the dosage which is a product of the intensity of the UV light and the exposure time. It is usually measured in microjoules per square centimeter, or equivalently as microwatt seconds per square centimeter ($\mu$W·s/cm2).

For example, for the *Escherichia coli* organism, commonly known as *E. coli*, a UV dose of 6600 $\mu$W·s/cm2 is recommended. The same dosage is recommended for the influenza virus ("flu") and *Staphylococcus aureus* ("staph").

Different sources which may provide UV light include low-pressure mercury lamps, medium pressure mercury lamps, light emitting diodes (LEDs), xenon flash lamps and deuterium lamps.

According to one embodiment of the present invention a chip sanitizing device comprises an area that is substantially enclosed and includes a sanitizing unit comprising a germicidal bulb and a power source. One or more chips is placed within the device and after the germicidal bulb is activated the one or more chips is sanitized.

According to a further embodiment of the present invention a germicidal bulb that emits UV in the optimal range is used to sanitize the chips housed on a casino chip rack. The embodiment further comprises a casino chip rack that sits upon a housing and where the slots holding the chips have been altered to contain holes to allow UV light to pass to the chips from within the housing. The embodiment may further comprise a sanitizing unit stored within the housing comprising one or more germicidal bulbs, ballasts, a power source and optionally a fan.

According to another embodiment of the present invention a cover is adapted to sit atop a chip rack as if it were a lid. The cover may be of any size or shape and substantially covers the exposed area of a chip rack. Within the cover is a sanitizing unit is stored comprising one or more germicidal bulbs, ballasts, a power source and a fan.

DETAILED DESCRIPTION OF SOME EMBODIMENTS OF THE INVENTION

The inventions are described in sufficient detail for a person skilled in the art to make and use the inventions. The inventions are described by reference to exemplary embodiments including devices and methods. The inventions, should not be limited to these embodiments, but may also include other apparatuses, and methods (not specifically described) in accordance with the inventions.

FIGS. 1-6 show different views of one embodiment of the present invention. As can be seen from FIG. 1 the invention comprises three components: a chip rack, a self-sanitizing layer and a housing.

Figure 4:
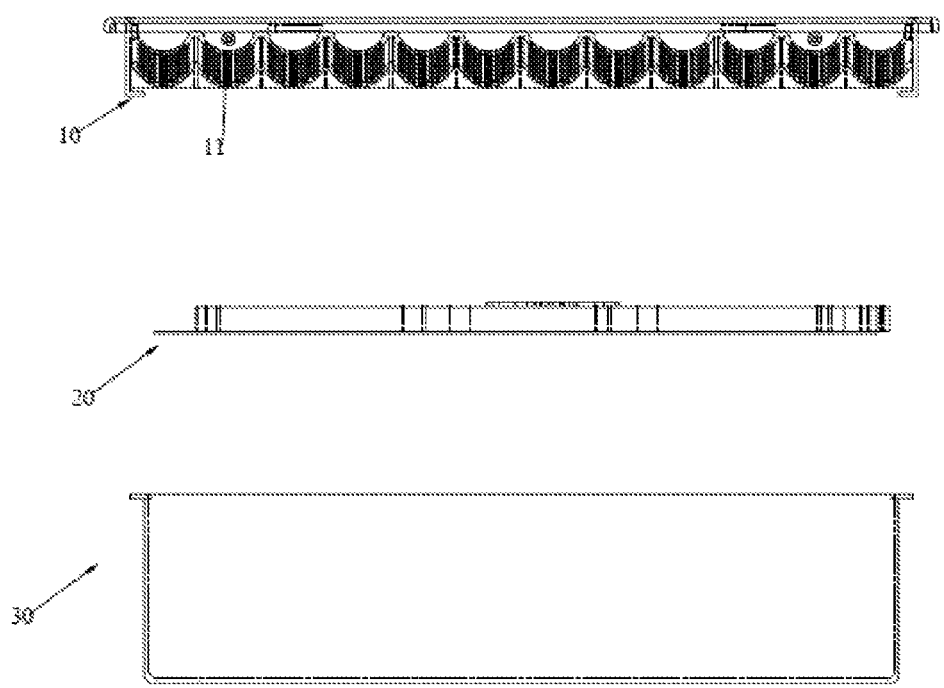
FIG. 4 is rear exploded elevational view thereof.
Figure 5:
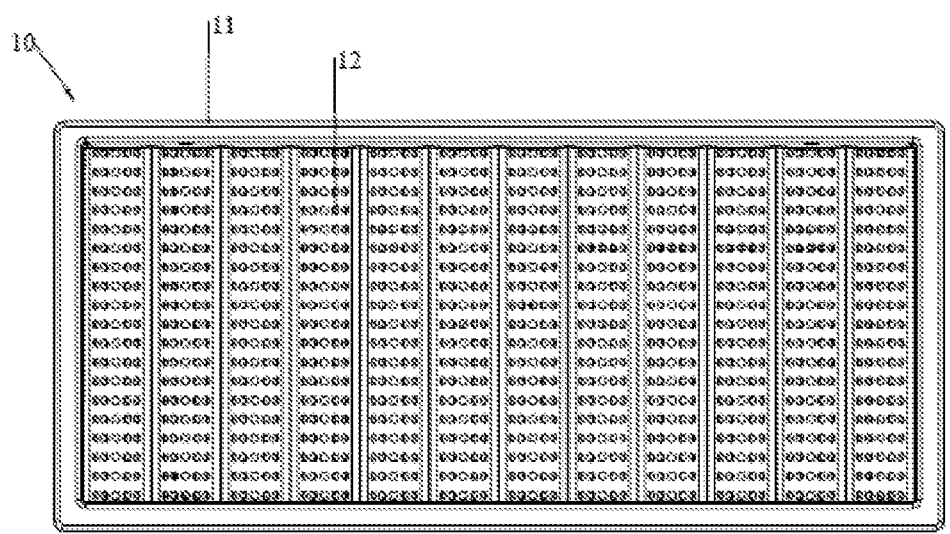
FIG. 5 is a top plan view thereof.

The first component is the chip rack, 10. The chip rack may be of any standard configuration and includes a plurality of chip slots 11. The slots are housed within four different walls. The length and width of the chip rack, and the number of chip slots are a matter of choice for the casino or manufacturer and not relevant to the embodiment disclosed. As shown in FIG. 4, the slots may be contoured in a semicircular fashion such that standard chips may be placed upright in the slots. The slots include openings or holes, 12, that allow light to pass through the slots. When the chip rack is viewed from above as in FIG. 5 these holes present a mesh like appearance. The number of holes in each slot is a matter of choice for the casino with more holes allowing a greater amount of light to pass through. As shown in FIG. 5, each row of each slot may have five holes but other number of holes are contemplated within the scope of the present invention. The slots may be made from different material including metal alloys and plastic. The back wall of the rack also includes two apertures 17 and 18. Apertures 17 and 18 are optionally included and may be used to fasten the chip rack with the housing described below through the use of screws.

Figure 6:
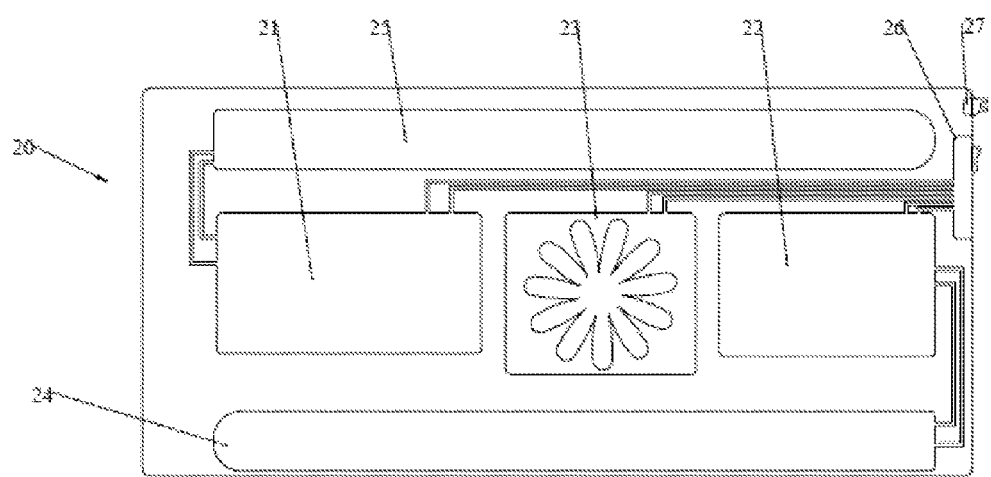
FIG. 6 is a top plan view of the sanitizing layer of an embodiment of a self sanitizing chip rack.

The second component of this embodiment is the sanitizing layer, 20 as shown in FIG. 6. It includes germicidal bulbs 24 and 25, fan 23, ballasts 21 and 22, junction box 26 and a power source 27. The power source 27 may be an alternating current (AC) power source. It is electrically connected to the junction box 26. The junction box is electrically connected to fan 23 and to ballasts 21 and 22. Each ballast is separately electrically connected to its respective germicidal bulb 24 or 25. When the power source is activated, line voltage is supplied to the ballast which is converted and supplied to its respective germicidal bulb. In a further embodiment, the germicidal bulbs, fan, ballasts, junction box and power source may be molded onto a tray made of a plastic or semi-plastic material.

When one or more of the germicidal bulbs is activated electromagnetic radiation is emitted in the direction of the chip rack and may pass through the holes 12 in slots 11. If any microorganisms lie on the surface of the chip, the UV may penetrate the outer cell membrane of these microorganisms, break the molecular bonds within the microorganismal DNA and disrupt the organism's ability to reproduce.

When the fan 23 is activated air may be circulated within the housing and thereby draw microorganisms into contact with the UV light emitted by the germicidal bulbs.

Figure 1:
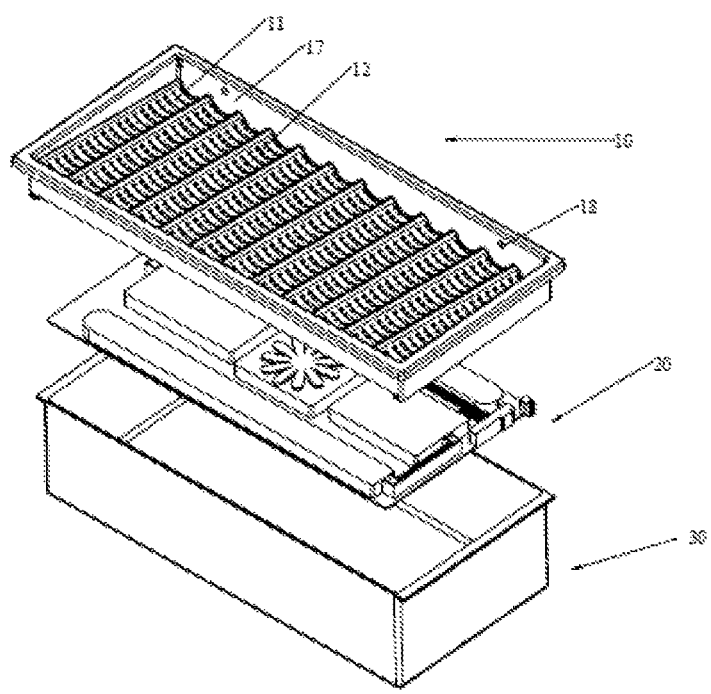
FIG. 1 is a left front perspective exploded view of an embodiment of the present invention.
Figure 2:
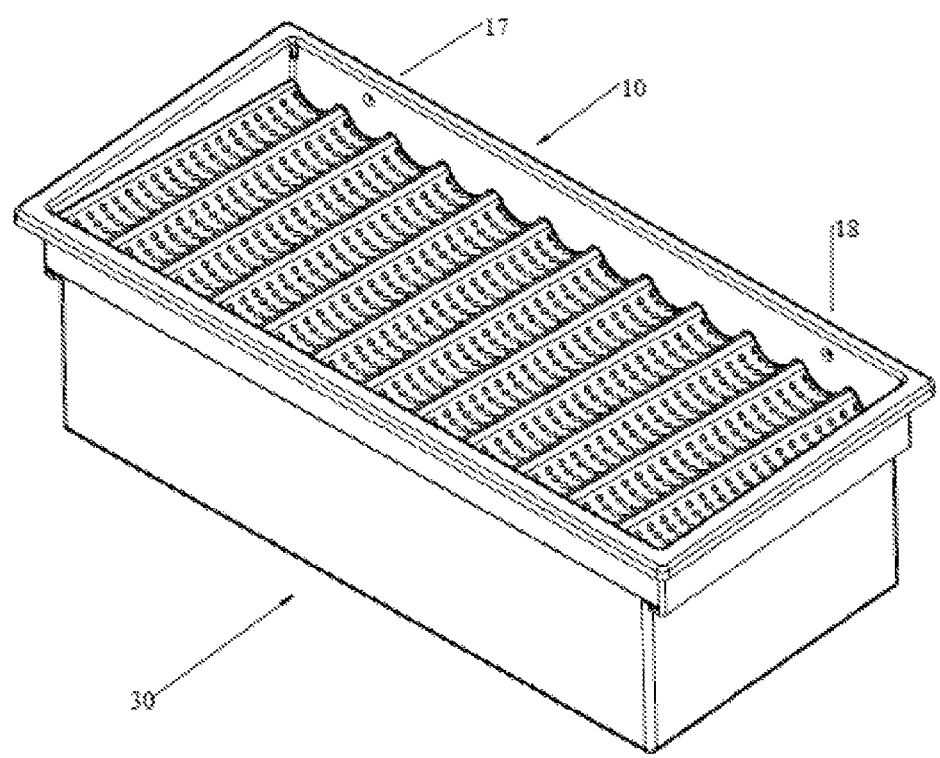
FIG. 2 is a left front perspective view thereof.
Figure 3:
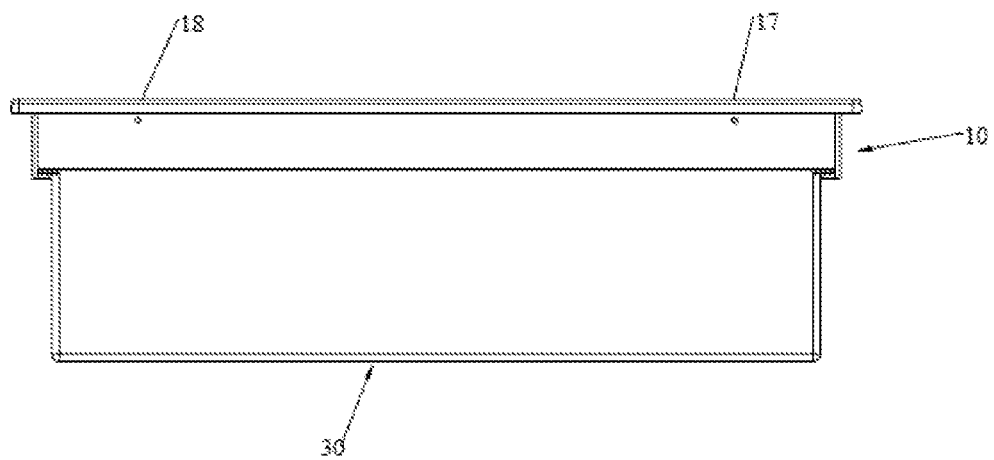
FIG. 3 is a rear elevational view thereof.

The third component of this embodiment is a housing unit 30 as shown in FIG. 1. The housing unit includes four walls and a base and is used to house the sanitizing layer 20. The four walls are perpendicularly attached to the base. The housing is dimensioned such that the sanitizing layer can fit within it and the chip rack 10 can sit atop it. Alternately, chip rack 10 may be fastened to housing unit 30 through the use of openings 17 and 18.

In a further embodiment, the sanitizing layer includes a power input, a power switch, a controller, a ballast, a germicidal bulb and a fan. The power input receives electrical power (such as DC from an internal battery or from an external source, or AC from an external source) used to operate the sanitizing layer. The power input can transfer the received power directly. The power input may also convert the received power into a form used by the other components of the sanitizing layer including the ballast, controller, germicidal bulb and fan. The power switch is an on/off switch used to activate the sanitizing layer. The controller may be configured to periodically activate the germicidal bulb through the ballast. The controller may be configured to periodically activate the fan. The controller can be implemented with analog components, digital component or both. The controller can also be programmable through a wireless or Bluetooth connection.

Figure 7:
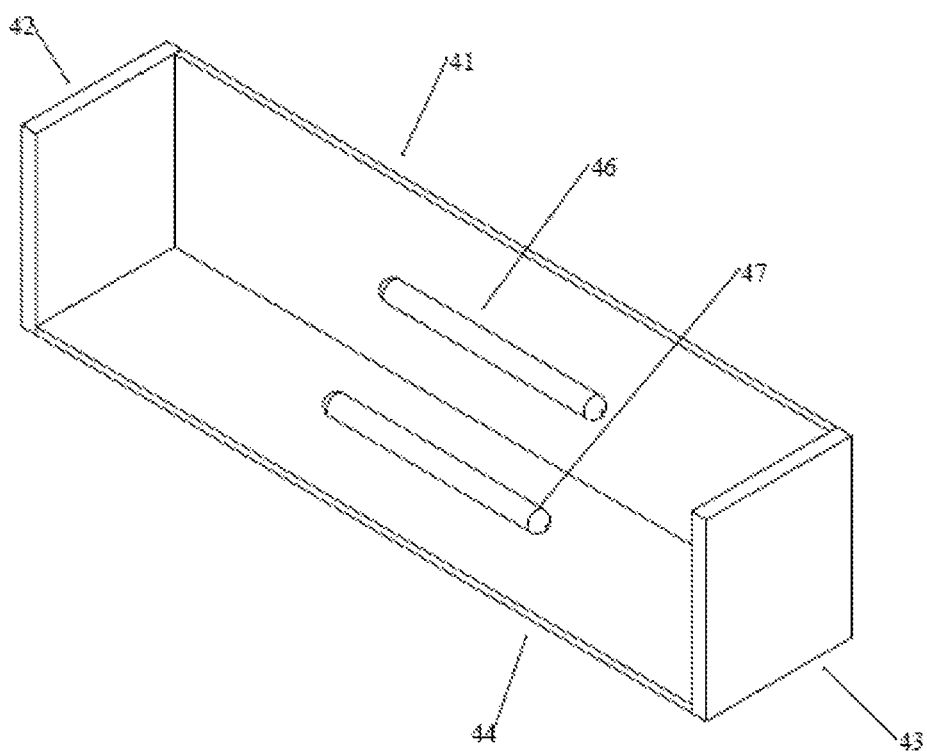
FIG. 7 is a left front perspective exploded view of an alternative embodiment of the present invention.

In a further embodiment the chip sanitizing device may be used to cover chips sitting atop a casino table. As shown in FIG. 7, the chip sanitizing device includes a top component, 41, a left side component, 42 a right side component 43 and a back component 44. The top component is perpendicular to the left, right and back side components and is rectangular in shape. Typically the top component has the same width and length as the area on the casino table where casino chips lay but may be within 5% in measurement of the width and length of the aforementioned area. Similarly the left and right side components are typically the same measurement as the width of the top component. The left and right components have their own thickness. Additionally the length of the back component is the same as the length of the top component. Various materials may be used to construct the top, left, right and back components. As would be understood by a person of skill in the art these include metal and semi-metal alloys, plastics, semi-plastic, ceramics and wood.

As further shown in FIG. 7 the covering includes a first and second germicidal bulb, 46 and 47, respectively. While not shown for simplicity sake, the covering also includes a fan, a first and second ballast, a junction box and a power source. The power source may be an alternating current (AC) power source. It is electrically connected to the junction box. The junction box is electrically connected to the fan and to the first and second ballasts. Each ballast is separately electrically connected to its respective germicidal bulb 46 or 47. When the power source is activated, line voltage is supplied to the ballast which is converted and supplied to its respective germicidal bulb. The germicidal bulbs, fan, ballasts, junction box and power source are housed within the covering. They may be attached to one or more of the left, right, back or top portions of the covering. They may be attached through the use of lamp support clip. In a further embodiment, the germicidal bulbs, fan, ballasts, junction box and power source may be molded onto a tray made of a plastic or semi-plastic material.

In a further embodiment, a chip sanitizing device comprises an area that is substantially enclosed and includes a sanitizing unit comprising a germicidal bulb and a power source. One or more chips is placed within the device and after the germicidal bulb is activated the one or more chips is sanitized.

In a further embodiment the germicidal bulb is configured to emit UV in the 253 nm to 265 nm range.

In a further embodiment the controller is programmed such that a dosage of 6600 µW·s/cm2 is delivered by the germicidal bulb.

In a further embodiment the controller is programmed to alternately activate the germicidal bulb for a first period followed by deactivating the germicidal bulb for a second period.

In a further embodiment, one of the walls of housing unit 30 may have an opening to allow wiring for the power source of the sanitizing layer 20 to extend outside of the housing.

In a further embodiment, the sanitizing unit may contain an additional light bulb that emits a light that can be more comfortably viewed by the human eye. This embodiment may alert customers that the chips are being sanitized and thereby provide a level of comfort.

In a further embodiment, a lid may be placed on top of chip rack 10. The lid may cover the chip rack so as to contain the ultraviolet light within the closed chip rack. Additionally the lid may be lined on its inner portion with a reflective material so as to reflect and intensify the ultraviolet light within the chip rack and increase the likelihood that the air within the chip rack and surfaces of chips will be sanitized. One such reflective material is specular aluminum although other material may also be suitable.

In a further embodiment, the invention comprises a lid that can substantially cover the exposed area of a chip rack. The lid may sit atop the chip rack or alternately may be fastened to it through the use of screws. The lid stores a sanitizing layer that comprises a germicidal bulb, a power source a ballast and a fan. Additionally the lid may be lined with a reflective surface within it such that UV radiation is directed to the chip rack that it covers.

While exemplary apparatus, systems and methods of the invention have been described herein, it should also be understood that the foregoing is only illustrative of a few particular embodiments with exemplary and/or preferred features, as well as principles of the invention, and that various modifications can be made by those skilled in the art without departing from the scope and spirit of the invention. Therefore, the described embodiments should not be considered as limiting of the scope of the invention in any way. Accordingly, the invention embraces alternatives, modifications and variations which fall within the spirit and scope of the invention as set forth herein and any equivalents thereto.

What is claimed is:

1. A system for sanitizing chips comprising:
   a chip rack housing defining a plurality of approximately semicircular slots adapted to support one or more casino chips in an upright fashion wherein the slots comprise one or more openings allowing UV-C light to pass through;
   a sanitizing layer placed below the chip rack housing comprising a UV-C light source, the UV-C light source comprising at least one germicidal bulb;
   a housing unit storing the sanitizing layer, the housing unit adapted to attach with the chip rack housing and comprising four walls perpendicularly attached to a base.

2. The system of claim 1, further comprising a ballast in electronic communication with the UV-C light source.

3. The system of claim 1, Therein the sanitizing later is molded onto a tray made of semi-plastic material.

4. The system of claim 1, wherein the germicidal bulb is configured to emit UV in the 253 nm to 265 nm range.

5. The system of claim 4 wherein the sanitizing layer further comprises a programmable controller electrically coupled to the at least one germicidal bulb and at least one fan.

6. The system of claim 5 wherein the programmable controller is programmed such that a dosage of 6600 IJW·s/cm2 is delivered by the at least one germicidal bulb.

7. The system of claim 6 wherein the sanitizing layer further comprises a non-UV light source electrically coupled to the programmable controller and the power source.

8. The system of claim 6 further comprising a lid adapted to substantially cover the chip rack, the lid comprised of opaque material and lined with specular aluminum.

9. A method for sanitizing chips comprising the steps of:
   a) placing one or more chips on the chip rack of the system of claim 1;
   b) activating the at least one germicidal bulb for a period of time.

10. A system for sanitizing chips comprising: a substantially enclosed area where chips may be inserted and a sanitizing unit comprising a UV-C light source, the UV-C light source comprising at least one germicidal bulb and a power supply, the at least one germicidal bulb electrically coupled to the power supply;
    wherein the sanitizing unit is molded onto a tray made of semi-plastic material, the tray comprising approximately semicircular slots adapted to support one or more casino chips in an upright fashion.

11. The system of claim 10 wherein the sanitizing unit further comprises at least one fan electrically coupled to the power supply.

12. The system of claim 11 wherein the substantially enclosed area comprises a covering adapted to substantially cover a chip rack.

13. The system of claim 11 wherein the substantially enclosed area comprises a left component a right component, a back component and a top component, wherein the top component is perpendicularly attached to the left component, the right component and the back component.

14. The system of claim 13 wherein the power source comprises a battery.

15. The system of claim 10, wherein the sanitizing section further comprises a programmable controller electrically coupled to the at least one germicidal bulb and wherein the programmable controller is programmed such that a dosage of 6600 µW·s/cm2 is delivered by the at least one germicidal bulb.

16. The system of claim 15 wherein the inner surface of one of the top back, left or right component is lined with specular aluminum.

17. A system for sanitizing chips comprising:
   a chip rack housing defining a plurality of approximately semicircular slots adapted to support one or more casino chips in an upright fashion wherein the slots comprise one or more openings allowing UV light to pass through;
   a UV light source comprising at least one germicidal bulb placed below the chip rack housing;
   a housing unit storing the UV light source, the housing unit adapted to attach with the chip rack housing.

18. The system of claim 17, wherein the chip rack housing has a flange portion that rests on the housing unit.

19. The system of claim 17, wherein the UV light is UV-C light.

20. The system of claim 17, wherein the housing unit is a cube with an open top, with the UV light source placed inside the housing unit, and the chip rack housing placed in proximity to the open top of the housing unit.

* * * * *